United States Patent
Nakanishi

(10) Patent No.: US 7,329,002 B2
(45) Date of Patent: Feb. 12, 2008

(54) OPHTHALMIC APPARATUS

(75) Inventor: Hiroyoshi Nakanishi, Hoi-gun (JP)

(73) Assignee: Nidek Co., Ltd., Gamagori (JP)

( * ) Notice: Subject to any disclaimer, the term of this patent is extended or adjusted under 35 U.S.C. 154(b) by 368 days.

(21) Appl. No.: 11/046,764

(22) Filed: Feb. 1, 2005

(65) Prior Publication Data

US 2005/0174534 A1    Aug. 11, 2005

(30) Foreign Application Priority Data

Feb. 3, 2004    (JP)    ............................. 2004-027320

(51) Int. Cl.
*A61B 3/00* (2006.01)
*A61B 3/10* (2006.01)

(52) U.S. Cl. ..................... 351/200; 351/212

(58) Field of Classification Search ................ 351/200, 351/212

See application file for complete search history.

(56) References Cited

U.S. PATENT DOCUMENTS

| 5,371,558 | A | * | 12/1994 | Kohayakawa | ............... | 351/208 |
| 5,500,696 | A | * | 3/1996 | Masuda et al. | .............. | 351/205 |
| 5,563,667 | A | * | 10/1996 | Isogai et al. | ................. | 351/208 |
| 5,822,034 | A | * | 10/1998 | Shimashita et al. | ......... | 351/212 |
| 5,907,388 | A | | 5/1999 | Fujieda | | |
| 5,909,269 | A | * | 6/1999 | Isogai et al. | ................. | 351/208 |
| 5,940,165 | A | | 8/1999 | Isogai et al. | | |

FOREIGN PATENT DOCUMENTS

| EP | 1 464 272 A1 | 10/2004 |
| JP | B2-1-19896 | 4/1989 |
| JP | A-06-007296 | 1/1994 |
| JP | A-10-108836 | 4/1998 |
| JP | A-10-193712 | 7/1998 |
| JP | A-10-216088 | 8/1998 |
| JP | A-2004-313758 | 11/2004 |

* cited by examiner

*Primary Examiner*—Jordan Schwartz
*Assistant Examiner*—James C Jones
(74) *Attorney, Agent, or Firm*—Oliff & Berridge, PLC.

(57) ABSTRACT

An ophthalmic apparatus capable of providing a printout of measurement results on a plurality of different eye characteristics in a required format. An ophthalmic apparatus capable of measuring a plurality of different eye characteristics of an eye of an examinee simultaneously or successively has a printer for providing a printout of a first measurement result on a first eye characteristic and a second measurement result on a second eye characteristic on predetermined paper, including a printing part which performs printing on the paper and a cutting part which cuts the paper, and a control part which controls the printing part to separately print the first measurement result in a first printing area of the paper and the second measurement result in a second printing area of the paper, and controls the cutting part to cut the paper so that the first printing area and the second printing area are separated.

8 Claims, 6 Drawing Sheets

```
------------0407------------
NAME                    M/F
DATE    20--. 7.22   14:07
VD=12.00mm

<R>       S        C       A
        -2.25    -0.00     0    6
        -2.25    -0.00     0    6
        -2.25    -0.00     0    7
       <-2.25    -0.00     0>

<L>       S        C       A
        -1.50    -0.25     8    8
        -1.50    -0.25     9    8
        -1.50    -0.25     8    8
       <-1.50    -0.25     8>

PD 65

<R>      mm       D      deg
<R1     8.41    40.25    161>
<R2     8.29    40.75     71>
<AVE    8.35    40.50       >
<CYL            -0.50    161>

<L>      mm       D      deg
<R1     8.44    40.00     10>
<R2     8.29    40.75    100>
<AVE    8.37    40.25       >
<CYL            -0.75     10>
```

FIG. 7

OPHTHALMIC APPARATUS

BACKGROUND OF THE INVENTION

1. Field of the Invention

The present invention relates to an ophthalmic apparatus capable of measuring a plurality of different eye characteristics of an eye of an examinee.

2. Description of Related Art

Conventionally, there is proposed a multifunction ophthalmic apparatus capable of measuring a plurality of different eye characteristics of an eye of an examinee simultaneously or successively by a single apparatus. In this kind of apparatus, a printer for providing a printout of measurement results on predetermined paper is included, and the measurement results on the respective eye characteristics of the eye of the examinee are printed on a piece of paper. FIG. 7 is a view showing an example of the printout thereof. On the paper from the top, an examination number, a space to include a name of the examinee, and an examination date and time are sequentially printed on the paper, and the measurement results on the respective eye characteristics (i.e., eye refractive power and a corneal shape (corneal radius of curvatures) in FIG. 7) are subsequently printed thereunder.

Incidentally, most ophthalmology clinics and the like adopt a policy of keeping the paper on which the measurement results are printed while sticking on patient charts, and there is a case where the measurement results on the different eye characteristics are stuck on separate positions on the patient charts. In such a case, as the measurement results on the respective eye characteristics are printed on a piece of paper in the conventional multifunction ophthalmic apparatus, troubles need be taken such as cutting the paper with a pair of scissors or the like, and writing down the examination number and the like thereon.

SUMMARY OF THE INVENTION

An object of the invention is to overcome the problems described above and to provide an ophthalmic apparatus capable of providing a printout of measurement results on a plurality of different eye characteristics in a required format.

To achieve the objects and in accordance with the purpose of the present invention, an ophthalmic apparatus capable of measuring a plurality of different eye characteristics of an eye of an examinee simultaneously or successively has a printer for providing a printout of a first measurement result on a first eye characteristic and a second measurement result on a second eye characteristic on predetermined paper, including a printing part which performs printing on the paper and a cutting part which cuts the paper, and a control part which controls the printing part to separately print the first measurement result in a first printing area of the paper and the second measurement result in a second printing area of the paper, and controls the cutting part to cut the paper so that the first printing area and the second printing area are separated.

In another aspect of the present invention, an ophthalmic apparatus capable of measuring a plurality of different eye characteristics of an eye of an examinee simultaneously or successively has a printer for providing a printout of a first measurement result on a first eye characteristic and a second measurement result on a second eye characteristic on predetermined paper, including a printing part which performs printing on the paper and a cutting part which cuts the paper, a mode selecting part for selecting a first mode for providing the printout while connecting the first and the second measurement results and a second mode for providing the printout while separating the first and second measurement results, and a control part which, when the second mode is selected, controls the printing part to separately print the first measurement result in a first printing area of the paper and the second measurement result in a second printing area of the paper, and controls the cutting part to cut the paper so that the first printing area and the second printing area are separated.

Yet, in another aspect of the present invention, an ophthalmic apparatus capable of measuring at least three kinds of different eye characteristics of an eye of an examinee simultaneously or successively has a printer for providing a printout of a first measurement result on a first eye characteristic, a second measurement result on a second eye characteristic, and a third measurement result on a third eye characteristic on predetermined paper, including a printing part which performs printing on the paper and a cutting part which cuts the paper, a mode selecting part for selecting a first mode for providing the printout while connecting all the first, second, and third measurement results, a second mode for providing the printout while separating all the first, second, and third measurement results, and a third mode for providing the printout while connecting two of the first, second, and third measurement results and separating the other one, and a control part which, when the second mode is selected, controls the printing part to separately print the first measurement result in a first printing area of the paper, the second measurement result in a second printing area of the paper, and the third measurement result in a third printing area of the paper, and controls the cutting part to cut the paper so that the first printing area, the second printing area, and the third printing area are separated.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 7 is a view showing an example of a conventional printout.

DETAILED DESCRIPTION OF THE PREFERRED EMBODIMENTS

Figure 1:
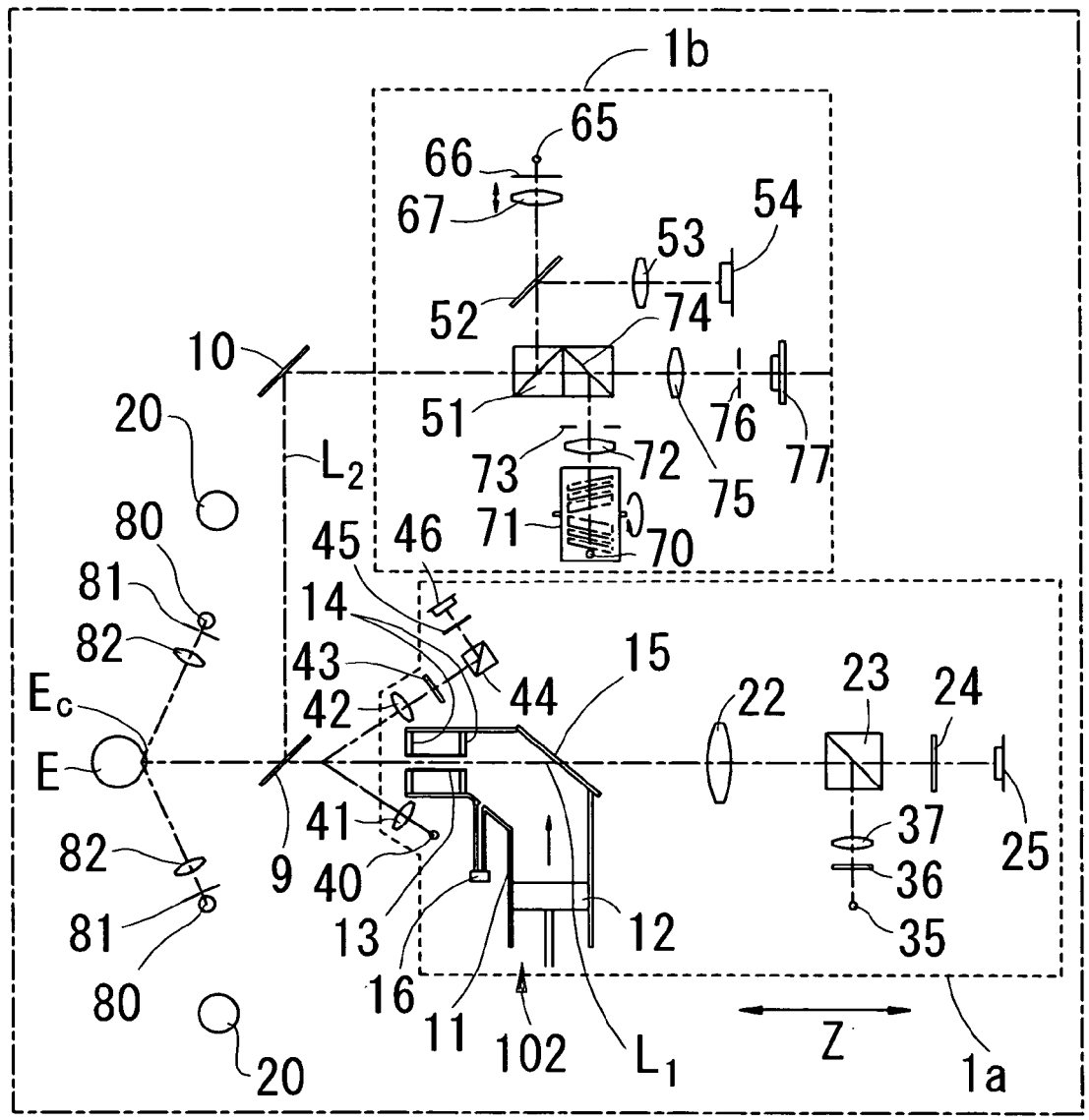
FIG. 1 is a view showing a schematic configuration of a measurement system of an ophthalmic apparatus consistent with the present invention.

A detailed description of one preferred embodiment of an ophthalmic apparatus embodied by the present invention is provided below with reference to the accompanying drawings. In this embodiment, a multifunction apparatus capable of measuring intraocular pressure, eye refractive power and a corneal shape (corneal radius of curvatures) will be taken as an example. FIG. 1 is a view showing a schematic configuration of a measurement system of an ophthalmic apparatus consistent with the present invention.

Inside a measurement unit 1, an intraocular pressure measurement part 1a for performing noncontact measurement of the intraocular pressure of an eye E of an examinee is arranged movably in a back/forth direction with reference to the eye E (the direction of a Z-arrow), and an eye refractive power/corneal shape measurement part 1b for measuring the eye refractive power and the corneal shape of the eye E is fixedly arranged above the measurement part 1a. Further, a reflection mirror 9 and a reflection mirror 10 are arranged.

At the time of intraocular pressure measurement, the mirror 9 is removed from between the eye E and a nozzle 13 in the measurement part 1a, and the measurement part 1a is moved in a direction toward the eye E so that the nozzle 13 faces the eye E. On the other hand, at the time of eye refractive power measurement and corneal shape measurement, the mirror 9 is inserted between the eye E and the nozzle 13, and the measurement part 1a is moved in a direction away from the eye E so as to retreat to the rear of the mirror 9.

Incidentally, while only the measurement unit 1 is illustrated in a configuration of the ophthalmic apparatus in FIG. 1, the apparatus is also provided with other elements such as a base for the apparatus, a mobile base which bears the measurement unit 1 thereon and is horizontally movable in back/forth and right/left directions on the base, a movement mechanism part for moving the measurement unit 1 in back/forth, right/left, and up/down directions with respect to the mobile base, and a face supporting unit fixedly arranged on the base for supporting a face (head) of the examinee. As those elements have little relevance to the present invention, description on a configuration thereof is omitted.

The measurement system arranged in the measurement unit 1 will be hereinafter described. Firstly, an air (fluid) blowing mechanism 102 in the measurement part 1a will be described. A cylinder 11 is for air compression. A piston 12 is moved inside the cylinder 11 by driving force of a rotary solenoid 103 described later. The air compressed inside the cylinder 11 by the movement of the piston 12 is blown through the nozzle 13 to a cornea Ec of the eye E. Two transparent glass plates 14 hold the nozzle 13. A transparent glass plate 15 is provided behind the nozzle 13. Behind the glass plate 15, optical systems for observation and alignment are arranged. A pressure sensor 16 detects pressure inside the cylinder 11.

Next, the optical systems in the measurement part 1a will be described. In this regard, when using the measurement part 1a (i.e., at the time of the intraocular pressure measurement), the mirror 9 is moved (removed) to a retreat position where it does not influence the intraocular pressure measurement.

Four infrared light sources 20 for anterior-segment illumination are arranged having a measurement optical axis L1 coincident with an axial line of the nozzle 13 as their center. An image of an anterior-segment of the eye E formed by the light sources 20 is transmitted through the glass plate 15, an objective lens 22, a dichroic mirror 23, and a filter 24, each arranged on the optical axis L1, to be picked up by a CCD camera 25 being an image-pickup element (these elements constitute an observation optical system). Besides, the dichroic mirror 23 has a property of transmitting infrared light and reflecting visible light. Additionally, the filter 24 has a property of not transmitting light from a light source 40 described later. The image of the anterior-segment of the eye E picked up by the camera 25 is displayed on a monitor 26 described later.

A visible light source 35 is for fixation target projection, and light from a fixation target 36 illuminated by the light source 35 is transmitted through a projection lens 37, the dichroic mirror 23, the objective lens 22, and the glass plate 15, to head for the eye E.

The infrared light source 40 is for detection of a deformation state of the cornea Ec, and the light therefrom is made into an approximately parallel light bundle by a collimator lens 41 to be projected onto the cornea Ec. An image of corneal reflection of the light source 40 is transmitted through a photo-receiving lens 42, a filter 43, a half mirror (or a reflection mirror) 44, and a pinhole plate 45, to be photo-received on a photo-detector 46. The filter 43 has a property of transmitting only the light from the light source 40. A corneal-deformation-state detection optical system (an intraocular pressure measurement optical system) constituted of these elements is arranged such that a photo-receiving amount on the photo-detector 46 is at the maximum when the cornea Ec is in a predetermined deformation state (a flat state).

Next, optical systems in the measurement part 1b will be described. When the measurement part 1b is used (i.e., at the time of the eye refractive power measurement and the corneal shape measurement), the mirror 9 is moved (inserted) to a measurement reference position between the eye E and the nozzle 13.

The image of the anterior-segment of the eye E formed by the light sources 20 is reflected by the mirror 9, and is transmitted through the mirror 10, a half mirror 51, a half mirror (or a dichroic mirror) 52, and an image forming lens 53, each arranged on a measurement optical axis L2 made coaxial with the optical axis L1 by the mirror 9, to be picked up by a CCD camera 54 being an image-pickup element (these elements constitute an observation optical system). The image of the anterior-segment of the eye E picked up by the camera 54 is displayed on the monitor 26 described later.

A visible light source 65 is for fixation target projection, and light from a fixation target 66 illuminated by the light source 65 is transmitted through a projection lens 67, the half mirror 52, the half mirror 51, the mirror 10, and the mirror 9, to head for the eye E. In addition, the projection lens 67 is moved in a direction of an optical axis, so that the eye E is fogged.

An infrared light source 70 is for the eye refractive power measurement. Light therefrom passes through slits provided in a rotation sector 71, and is transmitted through a projection lens 72, a diaphragm 73, a half mirror 74, the half mirror 51, the mirror 10, and the mirror 9, to be projected onto a fundus of the eye E while being scanned. The light reflected from the fundus is transmitted through the mirror 9, the mirror 10, the half mirror 51, the half mirror 74, a photo-receiving lens 75 and a diaphragm 76, and is photo-received on a photo-receiving part 77 provided with a plurality of pairs of photodetectors. Incidentally, for details of the optical system for the eye refractive power measurement, see U.S. Pat. No. 5,907,388 corresponding to Japanese Patent Application Unexamined Publication No. Hei10-108836.

Four infrared light sources 80 for the corneal shape measurement are arranged having the optical axis L1 as their center. Two of them are arranged in a horizontal direction of the apparatus, and the other two are arranged in a vertical direction of the apparatus, in order that each of their projection optical axes intersects at a predetermined angle with the optical axis L1. Light from the light sources 80 is transmitted through spot diaphragms 81 and collimating lenses 82 to be projected onto the cornea Ec. Images of corneal reflection of the light sources 80 are transmitted through the mirror 9, the mirror 10, the half mirror 51, the half mirror 52, and the image forming lens 53, to be picked up by the camera 54. Besides, for details of the optical system for the corneal shape measurement, see Japanese Patent Application Unexamined Publication No. Sho61-85920.

Figure 2:
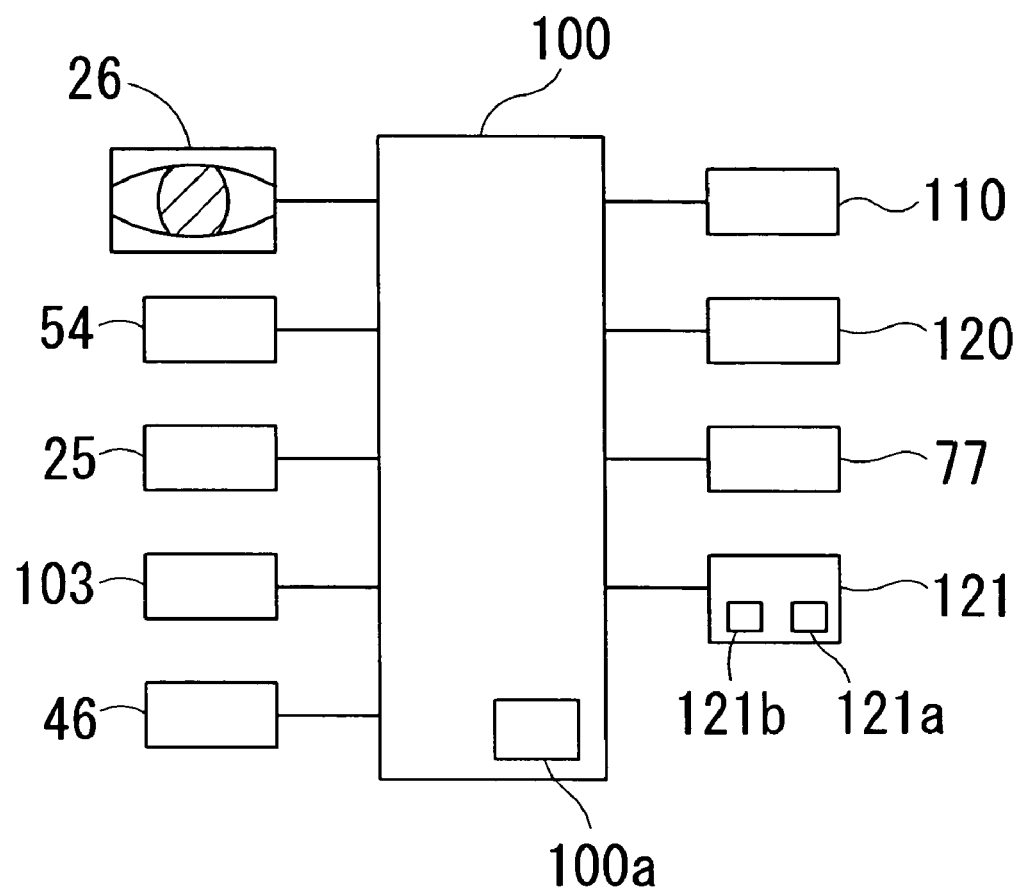
FIG. 2 is a view showing a schematic block diagram of a control system of the apparatus consistent with the present invention.
Figure 3:
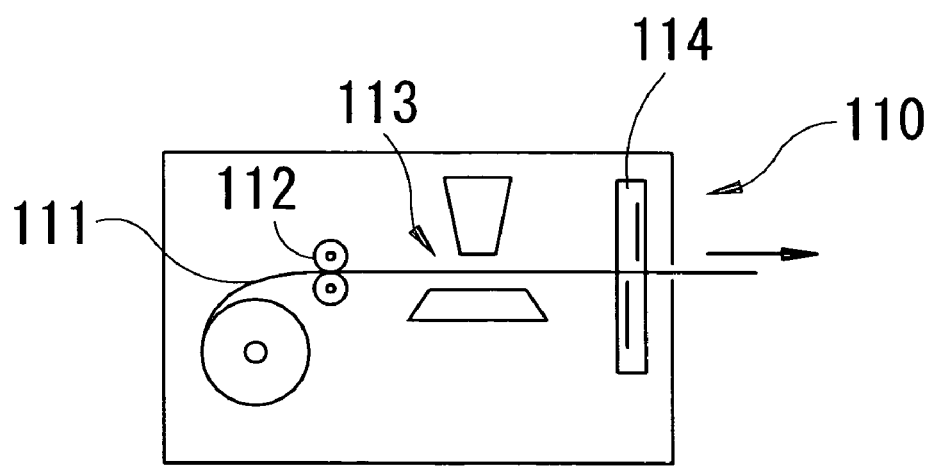
FIG. 3 is a view showing a schematic configuration of a printer.

FIG. 2 is a view showing a schematic block diagram of a control system of the apparatus consistent with the present invention. A control part 100 is connected with a printer 110 which provides a printout of measurement results on dedicated paper and a memory 120 which stores data such as the measurement results. As shown in FIG. 3, the printer 110 is constituted of paper 111, a paper-feeding part 112, a printing part 113, a cutting part 114, and the like. The printing part 113 prints the measurement results and the like on the paper 111 through right/left movements, and the paper-feeding part 112 feeds the paper each time one line has been printed. The cutting part 114 cuts the paper 111 at predetermined positions. The paper-feeding part 112, the printing part 113, and the cutting part 114 are driven and controlled by the control part 100.

Further, the control part 100 is connected with the monitor 26, the camera 25, the photo-detector 46, the rotary solenoid 103, the camera 54, the photo-receiving part 77, a switch part 121, and the like. The switch part 121 is provided with a printout mode selecting switch 121a for selecting (setting) a printout mode of the measurement results from one of a separated-output mode and a connected-output mode, and a PRINT switch 121b for inputting (emitting) an instruction signal for printout. In addition, the control part 100 is provided with a clock part 100a for indicating a present date and time.

In the ophthalmic apparatus having the aforementioned constitution, its operations will be described. The present apparatus includes a first measurement mode for performing only the eye refractive power measurement, a second measurement mode for performing only the corneal shape measurement, a third measurement mode for performing only the intraocular pressure measurement, a fourth measurement mode for successively performing the eye refractive power measurement and the corneal shape measurement, and a fifth measurement mode for successively performing the eye refractive power measurement, the corneal shape measurement and the intraocular pressure measurement. These measurement modes may be selected by an unillustrated measurement-mode selecting switch in the switch part 121. Besides, while the respective eye characteristics may be measured in any order, it is preferable that the intraocular pressure is measured last. This is because, if the intraocular pressure is measured first, an influence of the blow of the compressed air and the like possibly remains. Hereinafter, the fifth measurement mode will be described.

In the eye refractive power measurement and the corneal shape measurement, the mirror 9 is inserted between the eye E and the nozzle 13, and the image of the anterior-segment of the eye E is picked up by the camera 54. Once an alignment state of the measurement part 1b with the eye E falls within a predetermined permissible range, the control part 100 automatically controls to generate a trigger signal and obtain the eye refractive power based on output signals from the respective photodetectors in the photo-receiving part 77. In addition, the control part 100 controls to obtain a position of the image of corneal reflection of the light sources 80 and calculate the corneal shape, based on an output signal from the camera 54. Further, based on a travel (displacement) amount in the right/left direction of the measurement unit 1 at the time of measuring a right eye and a left eye of the examinee, a pupillary distance between the right and left eyes may also be obtained. The respective measurement results thereby obtained are stored in the memory 120.

In the fifth measurement mode, when the eye refractive power measurement and the corneal shape measurement satisfy a predetermined condition for measurement termination such that the predetermined number of measurement results are obtained respectively, the control part 100 automatically controls to generate a switching signal to the intraocular pressure measurement. Based on the switching signal to the intraocular pressure measurement, the control part 100 controls to move the measurement part 1a forward (in a direction toward the eye E), and thrust a tip of the nozzle 13 from a front surface of the measurement unit 1. At this time, the mirror 9 is removed from between the eye E and the nozzle 13 in conjunction with the movement of the measurement part 1a.

Once an alignment state of the measurement part 1a with the eye E falls within a predetermined permissible range, the control part 100 automatically controls to generate the trigger signal to drive the rotary solenoid 103. When the piston 12 is moved by the driving of the rotary solenoid 103, the air inside the cylinder 11 is compressed and blown through the nozzle 13 to the cornea Ec. The cornea Ec is gradually deformed by the blow of the compressed air, and when it reaches the flat state, the maximum amount of light enters the photo-detector 46. The control part 100 controls to calculate the intraocular pressure based on an output signal from the pressure sensor 16 and an output signal from the photo-detector 46. The measurement results thereby obtained are stored in the memory 120.

At the time of providing the printout of the obtained measurement results from the printer 110, the control part 100 reads out the respective measurement results on the eye refractive power, the corneal shape, and the intraocular pressure which are newly stored in the memory 120, and controls to provide the printout on the basis of a predetermined format. In the present embodiment, the printing is performed in the order of the eye refractive power (right/left), the corneal shape (right/left), and the intraocular pressure (right/left).

Here, in a case where the separated-output mode is selected by the switch 121a, when the instruction signal for printout from the switch 121b is inputted to the control part 100 upon completion of the measurement (the instruction signal for printout may be automatically generated taking a measurement completion signal as a trigger), the measurement results are started to be printed out from the printer 110.

Figure 4:
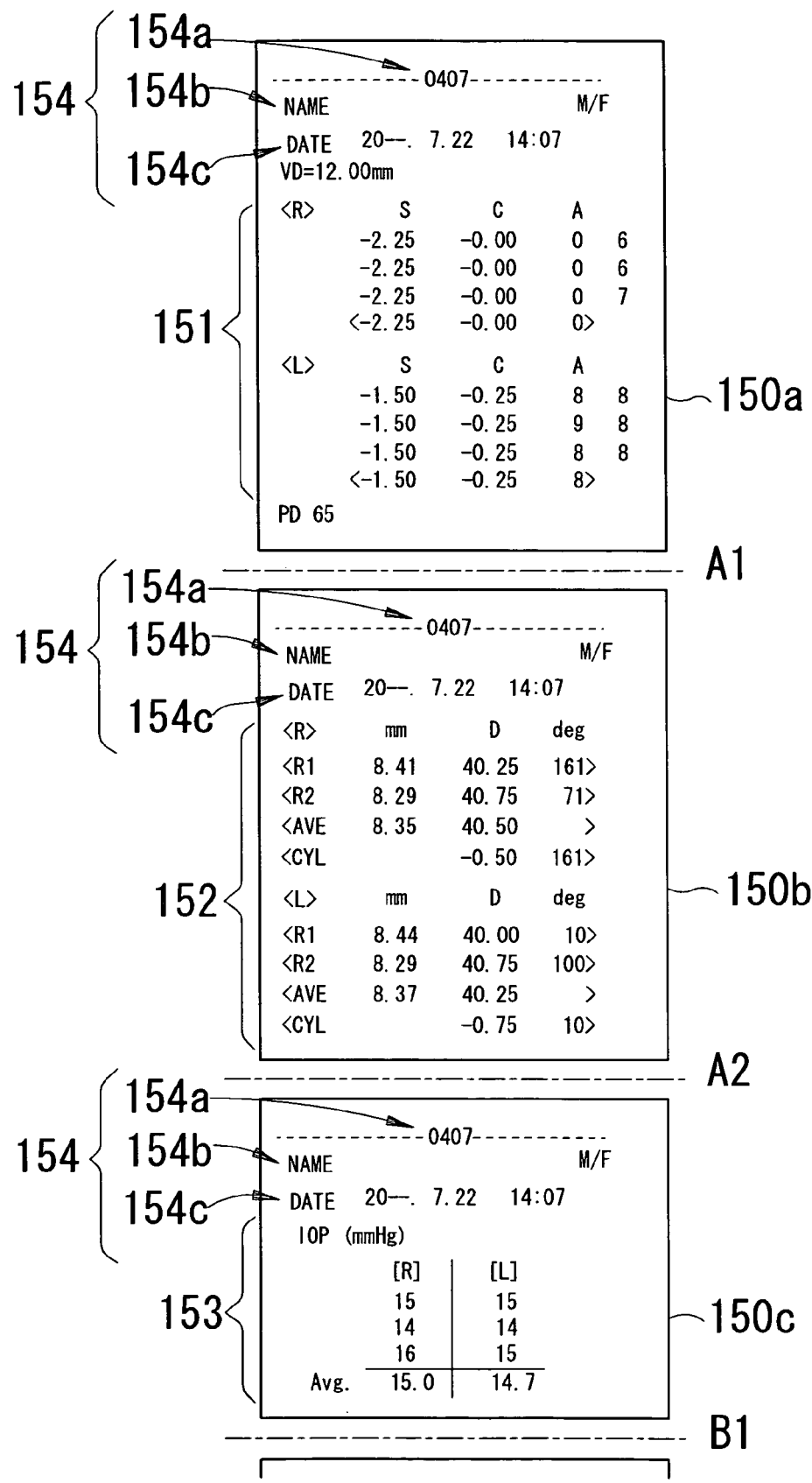
FIG. 4 is a view showing an example of a printout in a separated-output mode.

FIG. 4 is a view showing an example of a printout in the separated-output mode. On printing-paper portions (printing areas) 150a, 150b, and 150c which are cut and separated, an eye refractive power (hereinafter referred to as "R") measurement result 151, a corneal shape (hereinafter referred to as "K") measurement result 152, and an intraocular pressure (hereinafter referred to as "T") measurement result 153 are respectively printed. To be more specific, printed on the printing-paper portion 150a as the R measurement result 151 are measurement values obtained through three times of measurement of the eye refractive power (S (spherical power), C (astigmatic (cylindrical) power), and A (an astigmatic axial angle)) and their average values, and the like for the respective right and left eyes. Printed on the printing-paper portion 150b as the K measurement result 152 are measurement values of corneal radius of curvatures R1, R2 and their average value, values where the corneal radius of curvatures R1, R2 are converted into refractive power (diopter values) and their average value, and the like for the respective right and left eyes. Further, printed on the printing-paper portion 150c as the T measurement result 153 are measurement values obtained through three times of measurement of the intraocular pressure and their average value, and the like for the respective right and left eyes. In addition, on the printing-paper portion 150a, a pupillary distance PD between the right and left eyes and a vertex distance VD are printed.

Furthermore, on the respective printing-paper portions 150a, 150b, and 150c, common identification information 154 is printed above each of the measurement results. As the identification information 154, an examination number 154a utilized for distinguishing whose examination (measurement) is completed and the like is printed. The examination number 154a is increased by one when the instruction signal for printout is inputted or generated upon completion of the measurement. The examination number 154a is managed and determined by the control part 100. As the other identification information 154, a space 154b to include a name of the examinee, and an examination date and time 154c indicated by the clock part 110a are printed. The examination date and time 154c is determined as the time when the instruction signal for printout is inputted or generated. Thus, by printing the common identification information 154 on each of the printing-paper portions, the examination number, the examination date and time, and the like may be confirmed in each printing-paper portion. Therefore, the cut and separated printing-paper portions may be easily identified to enable accurate management and the like. Incidentally, the identification information is not limited to that provided above, and various information is included.

Besides, dashed lines A1, A2 and B1 in FIG. 4 indicate cutting positions of the paper 111 by the cutting part 114 in the printer 110. The line A1 indicates a boundary between the printing-paper portions 150a and 150b, and the line A2 indicates a boundary between the printing-paper portions 150b and 150c. The line B1 indicates a boundary between the printing-paper portion for the current measurement and a printing-paper portion for the next measurement (the examination number 154a is increased by one). These cutting positions are determined based on the format on the respective measurement results read out from the memory 120 and the setting of whether or not the paper is cut and separated (i.e., the setting of the printout mode).

If the constitution as above is employed, when the plurality of different eye characteristics are measured and the respective measurement results are printed out, the printout is provided while the paper is automatically separated for the respective measurement results. Therefore, in a case where the respective measurement results are stuck on separate positions on the patient charts, there is no need of cutting and separating with a pair of scissors or the like, and troubles may be saved. Besides, according to the above-mentioned separating method, the printing-paper portions are totally cut and separated at the cutting positions (boundaries); however, if the printing-paper portions are kept in a partly connected state (for example, in a perforated state, or in a state where a slight connecting portion is remained) so that an examiner may easily separate, the respective printing-paper portions are prevented from scattered. Such constitutions are also included in the separated state.

Figure 5:
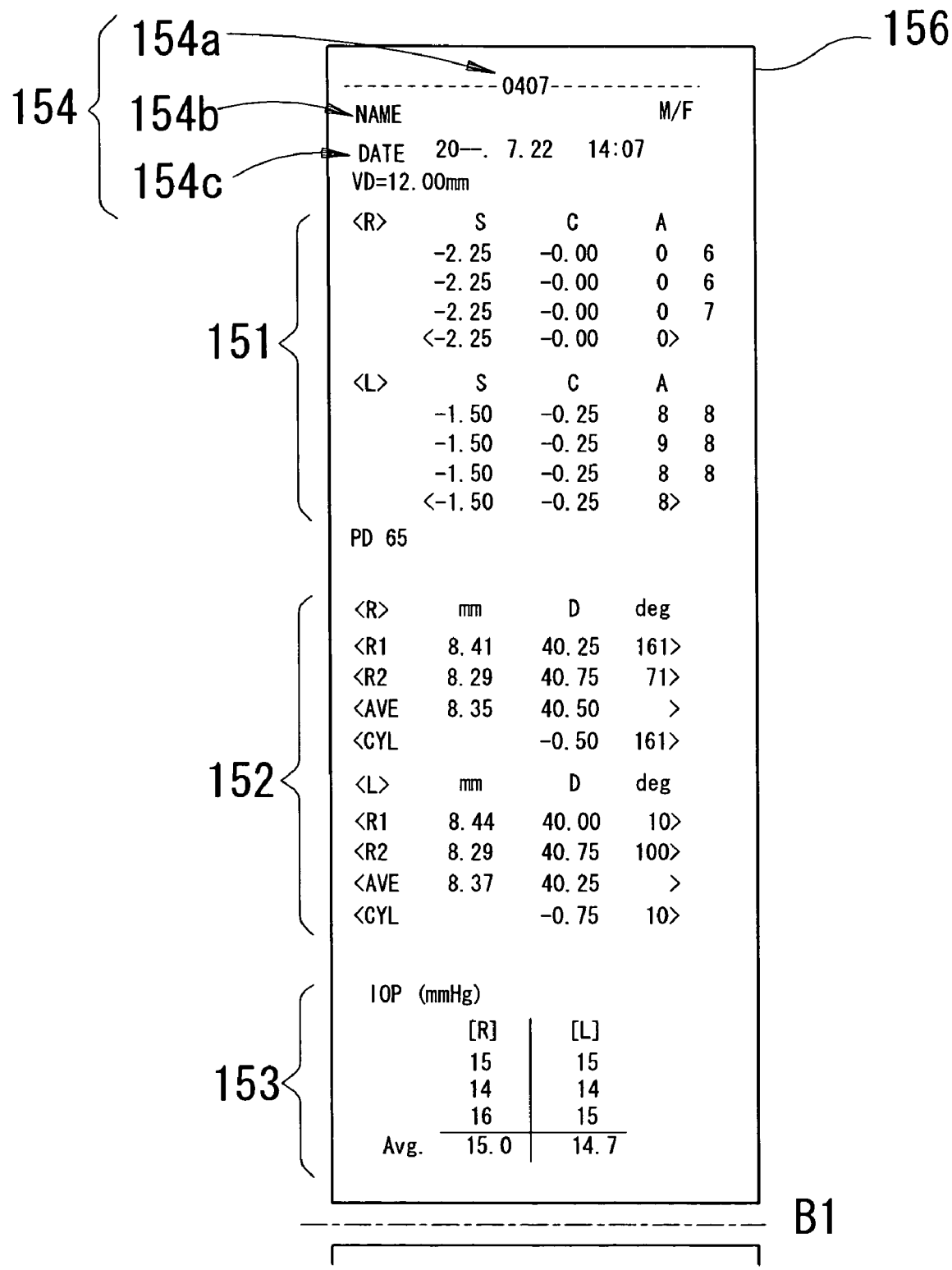
FIG. 5 is a view showing an example of a printout in a connected-output mode.

On the other hand, also in a case where the connected-output mode is selected by the switch 121a, when the switch 121b is depressed upon completion of the measurement (or the measurement completion signal is generated), the measurement results are started to be printed out from the printer 110. In such a case, as shown in FIG. 5, the R measurement result 151, the K measurement result 152, and the T measurement result 153 are printed on one printing-paper portion (printing area) 156 in a connected state, and the control part 100 drives the cutting part 114 only at the boundary line B1. Further, in the connected-output mode, the identification information 154 such as the examination number 154a, the space 154b to include the name of the examinee, and the examination date and time 154c are printed only above the R measurement result 151.

Incidentally, the eye characteristics to be measured are not limited to the eye refractive power, the corneal shape, and the intraocular pressure as above, and various eye characteristics are included.

Figure 6:
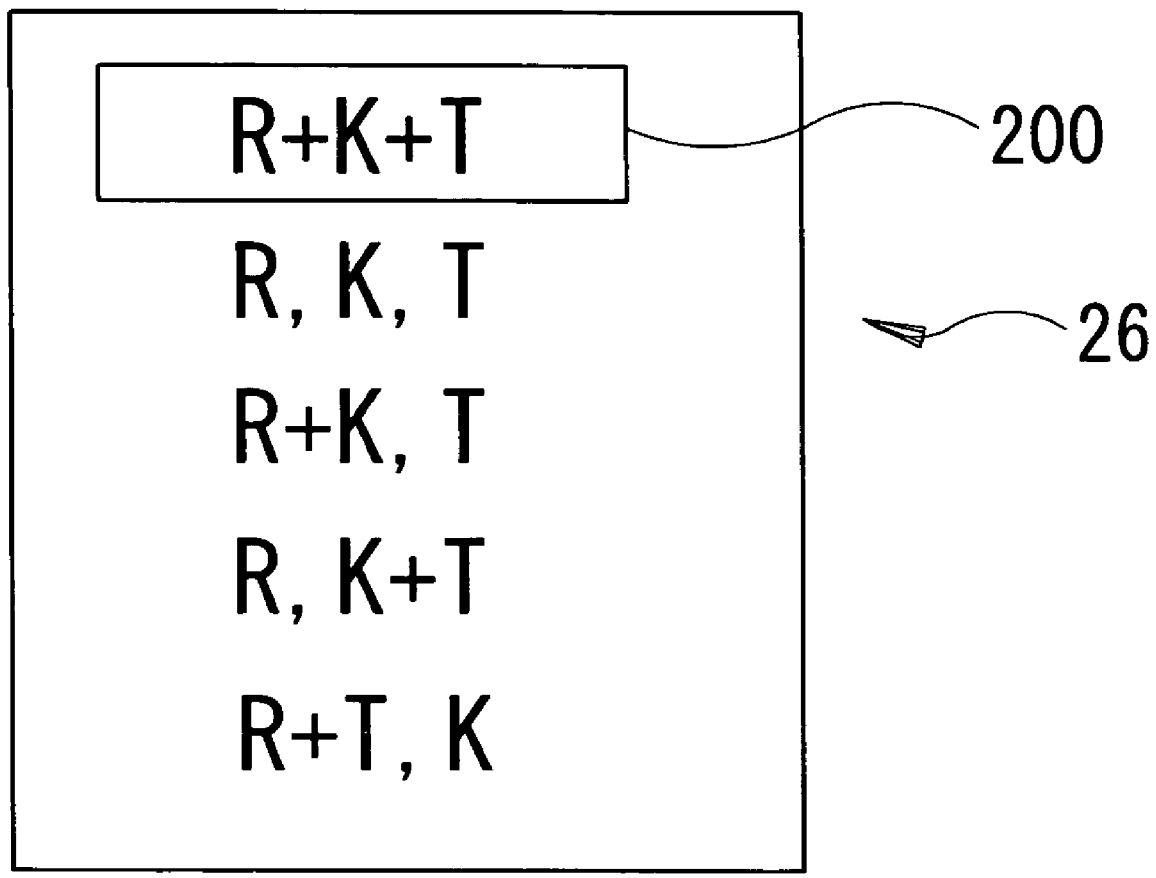
FIG. 6 is a view showing a screen example when setting a combination of a measurement result to be printed out while separated and a measurement result to be printed out while connected.

Next, in the apparatus capable of measuring more than three kinds of eye characteristics as the present embodiment, a combination of the measurement result to be printed out while separated and the measurement result to be printed out while connected may be set in more detail. FIG. 6 is a view showing a screen example for setting the combination thereof. When "R+K+T" is selected by moving a selecting cursor 200 through operation of an unillustrated switch in the switch part 121, the respective R, K and T measurement results are printed out in a connected state. Further, when "R,K,T" is selected, the respective R, K and T measurement results are printed out in a separated state. Furthermore, when "R+K,T" is selected, the R and K measurement results are printed out in a connected state and only the T measurement result is printed out in a separated state. Same applies to the other settings. In other words, on the setting screen, the measurement results linked with "+" are printed out in a connected state, and the measurement results linked with "," are printed out in a separated state. Thus, in a case where more than three kinds of measurement results are printed out, if the combination of separation and connection is made arbitrarily selectable, it becomes possible to cope with a large variety of patient charts.

Description has been given on a case where three kinds of eye characteristics: the eye refractive power; the corneal shape; and the intraocular pressure are measured. When one or two eye characteristics among them are newly measured, the printing and cutting by the printer 110 are controlled as provided below.

For example, in a case where the separated-output mode is set or the combination "R,K,T", "R,K+T", or "R+T,K" is selected (i.e., in a case where the R and K measurement results are printed out in a separated state), when only the eye refractive power and the corneal shape are measured after the previous printout, new measurement results on the eye refractive power and the corneal shape are stored in the memory 120. When the instruction signal for printout is generated at this stage, based on the newly stored measurement results on the eye refractive power and the corneal shape, the control part 100 controls to print out only the printing-paper portions 150a and 150b in FIG. 4. Since the measurement result on the intraocular pressure is not newly stored in the memory 120, the printing-paper portion 150c is not printed out.

On the other hand, in a case where the connected-output mode is set or the combination "R+K+T" or "R+K,T" is selected (i.e., in a case where the R and K measurement results are printed out in a connected state), when the instruction signal for printout is generated at the stage where only the eye refractive power and the corneal shape are measured after the previous printout, the R measurement result 151 and the K measurement result 152 are printed out on one printing-paper portion in a connected state. That is to say, the printout is provided while omitting the part of the T measurement result 153 in the printing-paper portion 156 in FIG. 5.

Incidentally, the measurement results stored in the memory 120 are cleared at the stage where the instruction signal for printout is inputted or generated and the measurement results are printed out, or at the stage where the new measurement of any eye characteristic is performed after the instruction signal for printout is inputted or generated (or after the printout).

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus capable of measuring a plurality of different eye characteristics of an eye of an examinee simultaneously or successively, the apparatus comprising:
    a printer for providing a printout of a first measurement result on a first eye characteristic and a second measurement result on a second eye characteristic on predetermined paper, including a printing part which performs printing on the paper and a cutting part which cuts the paper;
    a mode selecting part for selecting a first mode for providing the printout while connecting the first and the second measurement results, and a second mode for providing the printout while separating the first and second measurement results; and
    a control part which, when the second mode is selected, controls the printing part to separately print the first measurement result in a first printing area of the paper and the second measurement result in a second printing area of the paper, and controls the cutting part to cut the paper so that the first printing area and the second printing area are separated.

2. The ophthalmic apparatus according to claim 1, wherein, when the second mode is selected, the control part controls the printing part to print common identification information in the first and second printing areas, respectively.

3. The ophthalmic apparatus according to claim 2, wherein the control part controls to print the identification information determined based on input or generation of an instruction signal for printout.

4. The ophthalmic apparatus according to claim 1, further comprising a storing part capable of storing the first and second measurement results, and
    wherein the control part controls the printing part and the cutting part based on a measurement result newly stored in the storing part at the time of the input or generation of the instruction signal for printout and the selected printout mode.

5. An ophthalmic apparatus capable of measuring at least three kinds of different eye characteristics of an eye of an examinee simultaneously or successively, the apparatus comprising:
    a printer for providing a printout of a first measurement result on a first eye characteristic, a second measurement result on a second eye characteristic, and a third measurement result on a third eye characteristic on predetermined paper, including a printing part which performs printing on the paper and a cutting part which cuts the paper;
    a mode selecting part for selecting a first mode for providing the printout while connecting all the first, second, and third measurement results, a second mode for providing the printout while separating all the first, second, and third measurement results, and a third mode for providing the printout while connecting two of the first, second, and third measurement results and separating the other one; and
    a control part which, when the second mode is selected, controls the printing part to separately print the first measurement result in a first printing area of the paper, the second measurement result in a second printing area of the paper, and the third measurement result in a third printing area of the paper, and controls the cutting part to cut the paper so that the first printing area, the second printing area, and the third printing area are separated.

6. The ophthalmic apparatus according to claim 5, wherein, when the second mode is selected, the control part controls the printing part to print common identification information in the first, second, and third printing areas, respectively.

7. The ophthalmic apparatus according to claim 6, wherein the control part controls to print the identification information determined based on input or generation of an instruction signal for printout.

8. The ophthalmic apparatus according to claim 5, further comprising a storing part capable of storing the first, second, and third measurement results, and
    wherein the control part controls the printing part and the cutting part based on a measurement result newly stored in the storing part at the time of the input or generation of the instruction signal for printout and the selected printout mode.

* * * * *